United States Patent [19]
Bruns et al.

[11] Patent Number: 4,755,517

[45] Date of Patent: Jul. 5, 1988

[54] DERIVATIVES OF XANTHINE, PHARMACEUTICAL COMPOSITIONS AND METHODS OF USE THEREFOR

[75] Inventors: Robert F. Bruns, Ann Arbor; Harriet W. Hamilton, Chelsea, both of Mich.

[73] Assignee: Warner-Lambert Company, Morris Plain, N.J.

[21] Appl. No.: 892,538

[22] Filed: Jul. 31, 1986

[51] Int. Cl.$^4$ ................ C07D 239/36; A61K 31/52
[52] U.S. Cl. ................ 514/263; 544/266; 544/267; 544/272
[58] Field of Search ............ 544/267, 266, 272; 514/263

[56] References Cited

U.S. PATENT DOCUMENTS

| | | | |
|---|---|---|---|
| 3,624,215 | 11/1971 | Steden | 424/253 |
| 3,624,216 | 11/1971 | Steden | 424/253 |
| 4,031,218 | 6/1977 | El-Antably | 544/267 |
| 4,089,959 | 5/1978 | Dianund | 424/253 |
| 4,233,303 | 11/1980 | Bergstrand et al. | 544/267 |
| 4,364,962 | 12/1980 | Berne et al. | 424/253 |
| 4,452,788 | 6/1984 | Bristol et al. | 424/250 |
| 4,469,698 | 9/1984 | Philipossian | 424/253 |
| 4,593,095 | 6/1986 | Snyder et al. | 544/272 |

FOREIGN PATENT DOCUMENTS

| | | |
|---|---|---|
| 898946 | 6/1984 | Belgium . |
| 149578 | 6/1985 | European Pat. Off. . |
| 003874 | 8/1985 | European Pat. Off. . |
| 31722 | 4/1964 | Fed. Rep. of Germany . |
| 3406275 | 2/1984 | Fed. Rep. of Germany . |
| 2075505 | 11/1981 | United Kingdom . |

OTHER PUBLICATIONS

Pharmcol. (1985) 330:212–221.
J. Med. Chem. (1985) 28:1334–1340.
J. Med. Chem. (1985) 28:1071–1079.
J. Med. Chem. (1985) 28:487–492.
Proceedings of the Federation of American Society for Experimental Biology, vol. 45, No. 4, 3/5/86 (Abst.).
Jerry March Textbook, "Advanced Organic Chemistry, Reactions, Mechanisms, and Structures", p. 42 from Chapter 2.

Primary Examiner—Nicholas S. Rizzo
Attorney, Agent, or Firm—Joan Thierstein

[57] ABSTRACT

The present invention is a novel disubstituted derivative of xanthine, pharmaceutical composition and method of use therefor. Activity of the novel xanthine includes particularly cognition activation.

9 Claims, No Drawings

DERIVATIVES OF XANTHINE, PHARMACEUTICAL COMPOSITIONS AND METHODS OF USE THEREFOR

BACKGROUND OF THE INVENTION

The present invention is various novel analogs of xanthine. Additionally, the invention is pharmaceutical compositions having as the active compound the novel analogs of xanthines. The invention is also methods of use of the analogs. The use of the analogs of the present invention relates particularly to a desirable affinity at adenosine receptors, particularly the $A_1$ receptor. That is, the analogs are adenosine receptor antagonists. Thus, the analogs, for example, provide activity for use as a CNS stimulant, cognition activator, and bronchodilator.

Xanthines and particularly alkyl derivatives thereof, having adenosine receptor affinity are well known for use to treat cardiovascular diseases, as bronchodilators, and/or as psychotropic agents and CNS stimulants, as well as diuretics, and for the treatment of migraines or allergies.

More recently dialkenyl derivatives of xanthines are also found to have activity as adenosine antagonists. See copending U.S. Ser. No. 864,939 filed May 20, 1986, now abandoned.

The copending Application No. 885,057 filed July 14, 1986 which is a continuation in part of U.S. Ser. No. 864,939 filed May 20, 1986 now abandoned is hereby incorporated by reference having a review of related references also appropriate in the present invention. However, neither the copending U.S. Ser. No. 864,939 nor the references cited therein make obvious to one of ordinary skill a combination of substituents of the analogs of the present invention.

SUMMARY OF THE INVENTION

Accordingly, the present invention relates to a compound of the formula I

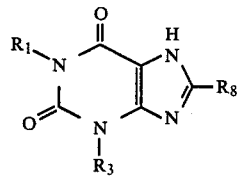

and the pharmaceutically acceptable salts thereof; wherein $R_1$ and $R_3$ are the same or different and are hydrogen, lower alkyl, hydroxyloweralkyl, or alkoxyloweralkyl;

$R_8$ is dihydroxyalkyl; or

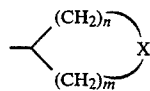

wherein X is oxygen, sulfur, or $NR_9$ wherein $R_9$ is hydrogen, lower alkyl or acyl of from two to six carbons;
n and m may be the same or different and are integers of from zero to five with the proviso that n and m together are of from one to four when X is oxygen and of from three to four when X is sulfur or $NR_9$.

Preferred compounds of the formula I compounds herein are the compounds wherein $R_1$ and $R_3$ are the same and being propyl, $R_8$ is oxygen or sulfur, n is zero or one and m is two or three. Further, the most preferred compounds are, therefore, 1,3-dipropyl-8-(2-tetrahydrofuranyl) xanthine; 1,3-dipropyl-8-(3-tetrahydrofuranyl) xanthine; or 1,3-dimethyl-8-(3-tetrahydrothienyl) xanthine.

The present invention also relates to a pharmaceutical composition for treating cognitive dysfunction, such as alzheimers disease or attention deficit syndrome, or asthma, comprising a cognition activator or antiasthma, or CNS stimulatory effective amount of a compound of the formula I as defined above. Finally, the present invention also relates to a method of treating a cognitive dysfunction, or asthma, in mammals, particularly humans, suffering therefrom by administering to such mammals the compound of formula I as defined above in unit dosage form.

DETAILED DESCRIPTION OF THE INVENTION

Lower alkyl of from one to six carbons such as methyl, ethyl, propyl, butyl, pentyl or hexyl and isomers thereof.

Hydroxyloweralkyl is a lower alkyl having at least one hydroxy substituent.

Alkoxyloweralkyl is a lower alkyl having at least one substituent that is an alkoxy of from one to six carbons such as methoxymethyl, ethoxymethyl, propoxymethyl, butoxymethyl, pentoxymethyl, hexoxymethyl, methoxyethyl and so on or isomers thereof. The isomers are understood and include, for example, 1-methoxyeth-1-yl, 1-methoxyprop-1-yl, 2-methoxyprop-1-yl, 2-methoxyprop-2-yl, and the like.

Acyl of two to six carbons is acetyl, propionyl and the like.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N- benzylphenethylamine; tris(hydroxymethyl)aminomethane; and the like. (See for example, "Pharmaceutical Salts," *J. Pharm. Sci.* (1977) 66(1):1–19.)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and the mixtures thereof. The individual isomers may be prepared or isolated by methods known in the art.

The processes for preparing the compounds of the present invention are shown in Scheme 1 and Scheme 2 hereinafter and also are described, generally, by process conditions known in the art or analogous to those known in the art. For example, the compounds of the present invention are generally prepared as disclosed in the application Ser. No. 885,057 which is the continuation in part of U.S. Ser. No. 864,939 filed May 20, 1986 as noted above.

Likewise the starting materials for the processes shown in Schemes 1 and 2 are readily available commercially, or can be prepared by either known methods or methods analogous to known methods.

Scheme 1

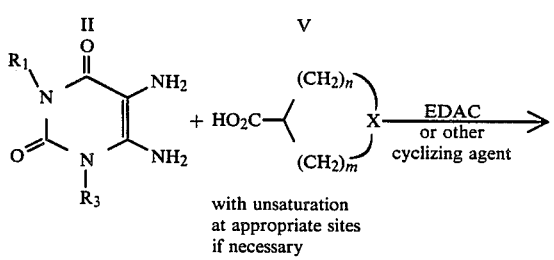

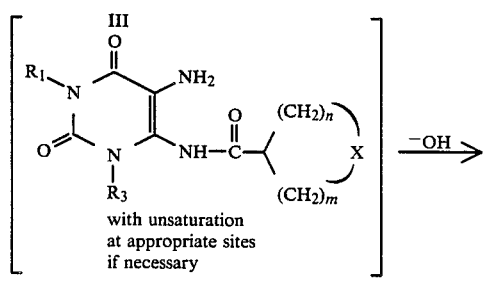

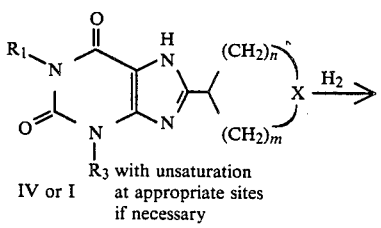

-continued
Scheme 1

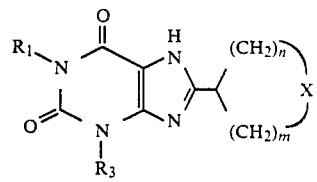

Scheme 2

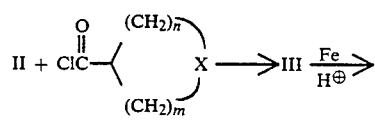

with unsaturation
at appropriate sites
if necessary

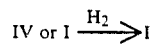

In Scheme 1 the known diaminouracil II wherein $R_1$ and $R_3$ as defined above is treated with an appropriate carboxylic acid of formula V wherein X and m and n are as defined above in the presence of a cyclizing agent such as a carbodiimide (e.g., ethyldimethylaminopropylcarbodiimide, EDAC), or carbonyldiimidazole, and the resulting aminoamide uracil of formula III wherein $R_1$, $R_3$ X, m and n are as defined above is cyclized under basic conditions to afford products of structure IV which is the compound I if no unsaturation is present in the moiety having X therein. The compound of formula V may have unsaturated carbon-carbon bonds present, such as is particularly shown by the Scheme $1_1$ hereinafter. Thus, on the other hand, when unsaturation is present in the moiety having X therein, known methods of hydrogenation yield the compound of formula I. Alternatively in Scheme 2 the compound of formula II as defined above can be treated with an appropriate acid chloride of formula VI wherein m, n and X are as defined above, in an inert solvent, usually in the presence of a base such as triethylamine. The resulting aminoamide uracil of formula III as defined above is then reductively cyclized using a metal such as iron in the presence of an acid such as sulfuric, hydrochloric, or the like, which affords product IV or I as defined above. Again in appropriate instances the moiety containing, X may have carbon-carbon unsaturation. That is, if structures V or VI contain sites of unsaturation, the products IV resulting from the reaction are then subjected to hydrogenation in the presence of a catalyst such as Raney nickel or Palladium on aluminum oxide or the like using known methods to afford the saturated product I.

More specifically the general reactions of Schemes 1 and 2 are illustrated in the following Scheme $1_1$. In these schemes the compounds of Structure $V_1$ or $VI_2$ shown below may or may not contain sites of unsaturation as appropriate. For example, the tetrahydrofuranyl xanthine $I_1$ may be prepared from the furanoic acid, which after cyclization is reduced to the product (see A of Scheme $1_1$). The sulfur analog of formula $I_2$ may be prepared by direct cyclization of the saturated tetrahydrothienyl carboxylic acid to give product I₂. (See B of Scheme 1₁).

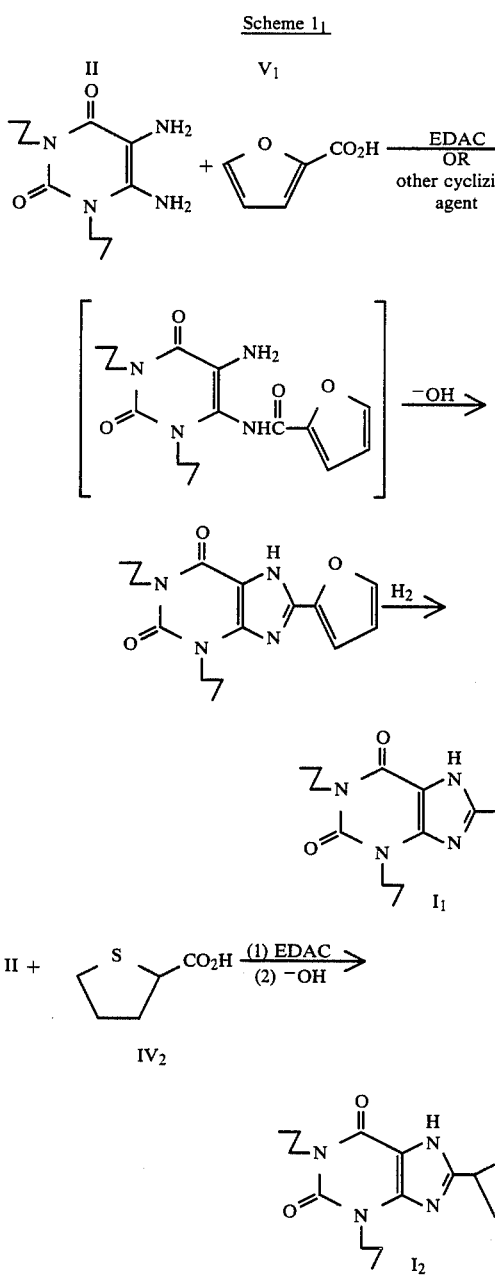

The products of each of the reactions described herein are isolated by conventional means such as extraction, distillation, chromatography, and the like.

The salts of compounds of formula I described above are prepared by reacting the appropriate base with a stoichiometric equivalent of the acid compounds of formula I, or of the appropriate acid with compounds of formula I having a base moiety.

The compounds of this invention may also exist in hydrated or solvated form.

The compounds of formula I have been found to have advantageous receptor affinities, particularly $A_1$ receptor affinities providing activity as bronchodilators, CNS stimulants, and/or cognition activators.

$A_1$ and $A_2$ affinities were determined in [$^3$H]-N$^6$-cyclohexyladenosine binding to rat whole brain membranes and [$^3$H]-NECA binding to rat striatal membranes, respectively, as previously described (Bruns, et al, Mol. Pharmacol. 29:331-346, 1986).

The IC$_{50}$ values (nM) for adenosine $A_1$ and $A_2$ receptor affinity are reported in the Table I.

TABLE I

| | Receptor Binding Data | |
|---|---|---|
| Example | RBA-1 (nM) | RBA-2 (nM) |
| 4 | 400 | 2000 |
| 3 | 28 | 4650 |
| 2 | 20 | 3100 |
| 1 | 2 | 622 |
| 5 | 88 | NT* |

*not tested

The above compounds may be compared to theophylline which binds the $A_1$ receptor at an IC$_{50}$ of 15,000 nM and the $A_2$ receptor at an IC$_{50}$ of 32,000 nm.

EVALUATION OF CENTRAL NERVOUS SYSTEM ACTIVITY

The purpose of this test is to identify drugs which antagonize the locomotor suppressant effects of $A_1$ and $A_2$ selective adenosine agonists in mice. Adenosine agonists produce inhibition of spontaneous exploratory activity in mice. This response has been demonstrated with the $A_1$ selective adenosine agonist CPA and the $A_2$ selective agonist CV-1808. The standard adenosine antagonist theophylline is active in this procedure by reversing the suppressant effects of both adenosine agonists. The procedure employs naive animals obviating the need for extensive training and precluding possible cumulative drug effects.

METHOD

Animals:

Male Swiss-Webster mice are used for this procedure. A minimum of 12 animals are used per dose including vehicle treated controls.

Drugs:

Compounds are dissolved or suspended in physiological saline containing Emulphor, 2-5%. Suspensions are ultrasonicated for 3 minutes. Drug doses are expressed as the active moiety and are administered intraperitoneally (IP) to mice in volumes of 10 ml/kg. CPA, N$^6$-cyclopentyladenosine, ($A_1$ agonist) and CV-1808, 2-anilinoadenosine, ($A_2$ agonist), are injected IP one hour before locomotor testing in respective doses of 2 and 8 mg/kg. The potential adenosine antagonist is injected 30 minutes before testing at the maximum dose which by itself has little or no effect on mouse locomotor activity.

Three control groups are utilized: a placebo control (vehicle treated mice used as an indication of base level locomotion); a reference control (a group of mice dosed with the antagonist alone to confirm the lack of locomotor response) and a positive control (a group of mice dosed with the agonist alone to demonstrate the inhibition of locomotion).

Procedure:

One hour after the agonist or vehicle injections and 30 minutes after the antagonist or vehicle injections, the mice are placed in darkened actophometers (3 mice/unit) and locomotor activity is monitored for 60 minutes. Activity counts are recorded automatically by a microcomputer.

Data Analysis:

Drug effects on locomotor activity are expressed as percent suppression relative to the vehicle treated (placebo) controls. The locomotor effect produced by the combination of agonist and antagonist (C) substrated from the locomotor suppressant effect of the agonist alone (B) is divided by the value for the agonist (B) and then multiplied by 100 to express the percent reversal. For example:

A. Theophylline, 10 mg/kg, alone produced locomotor stimulation (160% of placebo controls or −60% suppression).

B. CPA, 2 mg/kg, alone produced 94% suppression of locomotion.

C. Theophylline+CPA in combination produced stimulation (−42% locomotor suppression).

Then applying the formula: $(B-C)/B \times 100 = [94-(-60)]/94 \times 100 = 164\%$ reversal.

When theophylline was tested against CV-1808, 8 mg/kg, the data were as follows:

A. CV-1808 produced 83% suppression.

B. CV-1808 +theophylline produced 22% suppression.

Then: $(83-22)/83 \times 100 = 73\%$ reversal.

The data (values for "B" and "C") are then analyzed in a paired t-test, if the values are significantly different ($p<0.05$) from each other then the dose effect is given a reversal rating of "A"; if the data are insignificant ($p>0.05$) then the dose effect is given a rating of "N". In the above examples, the effects of theophylline against both CPA and CV-1808 were rated "A" (active as an antagonist).

The above example contains an important variant to the criterion set forth in the methods: the dose of theophylline selected produced a significant effect on locomotion (160% relative to control). This dose was selected on the basis of previous results which indicated little or no effect of 10 mg/kg. It is not uncommon to see variation in the locomotor effect of doses which are bordering on profound pharmacological responses, e.g., 30 mg/kg of theophylline on previous testing had produced marked stimulation (200% of control) while 10 mg/kg had produced 118% of control. In light of this possible variation in the locomotor response to the antagonist it is deemed important that the effect of the antagonist alone is shown in order to facilitate understanding how a reversal effect can be more than 100%.

In like manner the compounds of the present invention having $A_1$ and $A_2$ activity corresponding to theophylline are useful as a CNS stimulant.

Accordingly, the present invention also particularly includes a pharmaceutical composition for treating cognitive dysfunction such as Alzheimer's disease or attentional deficit disorders and a method for treating a cognitive dysfunction comprising administering to mammals, including humans, suffering therefrom either orally or parenterally the corresponding pharmaceutical composition. The composition contains a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 1 to 100 mg according to the particular application and the potency of the active ingredient. The compositions can, if desired, also contain other compatible therapeutic agents.

In therapeutic use as described above, the mammalian dosage range for a 70 kg subject is from 0.01 to 150 mg/kg of body weight per day or preferably 0.1 to 100 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention, but without, however, limiting it thereto.

EXAMPLE 1

1,3-Dipropyl-8-(3-tetrahydrothienyl)xanthine

The starting 1,3-dipropyl-8-(3-thienyl)xanthine is prepared in a manner analogous to that described in Example 2 hereinafter using 3-thiophenecarboxylic acid and 5,6-diamino-1,3-dipropyluracil, mp>250° C.

Analysis as $C_{15}H_{18}N_4O_2S$ (318.4); Calculated: C, 56.58; H, 5.70; N, 17.60. Found: C, 56.81; H, 5.74; N, 17.65.

The 1,3-dipropyl-8-(3-tetrahydrothienyl)xanthine is prepared as follows: To 1.1 g 1,3-dipropyl-8-(3-thienyl)xanthine in 50 ml THF is added 0.2 g 10% Pd/Al$_2$O$_3$, and the mixture reduced under a hydrogen atmosphere of 1000 lbs at 200° C. overnight. The reaction mixture is filtered, and the filtrate concentrated to give 0.55 g tan powder. Recrystallization from MeOH/CH$_2$Cl$_2$ gives 0.12 g crystals which are identical to starting material. The filtrate is concentrated and chromatographed (20% EtOAc 80% CH$_2$Cl$_2$ on SiO$_2$), to give 0.14 g product. This is determined to be a 1:2 mixture of the 1,3-dipropyl-8-(3-tetrahydrothienyl)xanthine and 1,3-dipropyl-8-(2-butyl)xanthine, mp 139°-145° C.

Analysis as $C_{15}H_{22}N_4O_2S$ (322.4); Calculated: C, 59.60; H, 7.78; N, 18.53; S, 3.50. Found: C, 60.05; H, 7.80; N, 18.10; S, 3.28.

EXAMPLE 2

1,3-Dipropyl-8-(2-tetrahydrofuranyl)xanthine 0.35 g 1,3-Dipropyl-8-(2-furanyl)xanthine is dissolved in 50 ml methanol, to which is added 0.5 g Raney nickel and the mixture reduced under a hydrogen atmosphere of 200 psi at 100° C. The mixture is then filtered, the filtrate concentrated to yield 0.34 g of the 1,3-dipropyl-8-(2-tetrahydrofuranyl)xanthine as a white solid, mp 155°-8° C.

Analysis as $C_{15}H_{22}N_4O_3$ (306.4); Calculated: C, 58.80; H, 7.24; N, 18.29. Found: C, 58.40; H, 7.42; N, 18.24.

The starting 1,3-dipropyl-8-(2-furanyl)xanthine is prepared as follows: 1.8 g (17 mmol) 2-furoic acid is added to a solution of 3.7 g, 5,6-diamino-1,3-dipropyluracil (17 mmol) (J. Am. Chem. Soc. (1954) 76 2798) in 50 ml water. The pH is adjusted to 5, then 3.2 g (17 mmol) ethyl-3-(3-dimethylamino) propylcarbodiimide is added. The pH is maintained between 5 and 6 using 1 N HCl. After 2 hours the pH stabilizes, and the solution is taken to pH 13 using 50% aqueous NaOH. The resulting mixture is refluxed for 30 minutes, activated carbon added, and filtered hot through celite. The filtrate is then extracted (3×100 ml CH$_2$Cl$_2$), dried (MgSO$_4$), and concentrated to yield 1.7 g yellow solid. This is recrystallized from methanol to give the 1,3-dipropyl-8-(2-tetrahydrofuranyl)xanthine as white needles, mp 246°-248° C. Analysis as $C_{15}H_{18}N_4O_3$ (302.3); Calculated: C, 59.59; H, 6.00; N, 18.53. Found: C, 58,86; H, 6.53; N, 19.45.

EXAMPLE 3

1,3-Dipropyl-8-(3-tetrahydrofuranyl)xanthine 1,3-Dipropyl-8-(3-tetrahydrofuranyl)xanthine is prepared by a process analogous to that described in Example 2 above, mp 177°-8° C.

Analysis as $C_{15}H_{22}N_4O_3 \cdot \frac{1}{2}H_2O$ (306.4); Calculated: C, 57.12; H, 7.35; N, 17.17. Found: C, 56.88; H, 6.94; N, 17.55.

The starting 1,3-dipropyl-8-(3-furanyl)xanthine is prepared by a process analogous to that described in Example 2 above using 3-furoic acid and 5,6-diamino-1,3-dipropyluracil, mp 244°-245° C.

Analysis Calculated: C, 59.59; H, 6.00: N, 18.53. Found: C, 59.70; H, 6.24; N, 18.45.

EXAMPLE 4

1,3-Dimethyl-8-(3-tetrahydrothienyl)xanthine 1,3-Dimethyl-8-(3-tetrahydrothienyl)xanthine is prepared in a manner analogous to that described in Example 2 above, mp 217°-219° C. Analysis as $C_{11}H_{14}N_4O_3$ (250.23); Calculated: C, 52.80; H, 5.64; N, 22.39. Found: C, 52.51; H, 5.73; N, 22.18.

The starting 1,3-dimethyl-8-(2-furanyl)xanthine is prepared in a manner analogous to that in Example 3 using 3-furoic acid and 5,6-diamino-1,3-dimethyluracil mp>300° C.

EXAMPLE 5

1,3-Dipropyl-8-(2-tetrahydrothienyl)xanthine

Uracil (1.75 g) is dissolved in 20 ml water plus 15 ml methanol. Tetrahydrothienylcarboxylic acid (1.02 g) is added in single portion and the pH adjusted to 5. There, EDAC (1.48 g) is added, and pH 5 maintained with 1N HCL for half hour until it stablizes. This is treated with 1N NaOH until a pH of 13 achieved, and the reaction mixture refluxed 14 hours. To this is added charcoal and the mixture filtered hot through Celite. It is then extracted with methylene chloride, the combined organic residue dried and concentrated to an oil. The aqueous layer is then neutralized (conc HCl), resulting in a white percipitate. This is extracted with methylene chloride, the combined organic residue dried and concentrated to give a solid. This solid is then recrystallized from methanol/methylene chloride to give the product, 1,3-dipropyl-8-(2-tetrahydrothienyl) xanthin. mp 224°–226° C.

The starting tetrahydrothienylcarboxylic acid is prepared as follows: To a stirred suspension of potassium bufoxide in THF is added TOSMIC (tosylmethylisocyanide, 3.9 g) at 7°–10° C. This is followed by 1.92 g thiolactam in 20 ml THF. After 5 minutes, 2 ml acetic acid is dripped in. The solution is concentrated, taken up in water, and extracted with methylene chloride. The combined organic residue is dried and concentrated, then 40 ml 2N HCl added and refluxed 12 hours. The solution is made basic and extracted with ether. The aqueous layer is taken to pH 1, extracted again with ether and these organics combined, dried, and concentrated to give the product tetrahydrothienylcarboxylic acid, mp 95°–98° C.

We claim:

1. A compound of the formula (I)

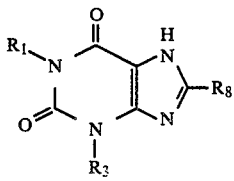

and the pharmaceutically acceptable salts thereof; wherein $R_1$ and $R_3$ are the same or different and are hydrogen, lower alkyl, hydroxyloweralkyl, or alkoxyloweralkyl; $R_8$ is dihydroxyalkyl; or

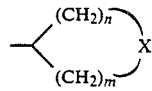

wherein X is oxygen, sulfur or $NR_9$ wherein
$R_9$ is hydrogen, lower alkyl or acyl of from two to six carbons; and n and m may be the same or different and
are integers of from one to five with the proviso that n and m together are of from one to four when X is oxygen and of from three to four where X is sulfur or $NR_9$.

2. A compound of claim 1 wherein $R_1$ and $R_3$ are the same and are propyl, X is oxygen or sulfur, n is zero or one and m is two or three.

3. A compound of claim 2 and being 1,3-dipropyl-8-(3-tetrahydrothienyl)xanthine.

4. A compound of claim 2 and being 1,3-dipropyl-8-(2-tetrahydrofuranyl)xanthine.

5. A compound of claim 1 and being 1,3-dimethyl-8-(3-tetrahydrofuranyl)xanthine.

6. A compound of claim 2 and being 1,3-dipropyl-8-(3-tetrahydrothienyl)xanthine.

7. A compound of claim 2 and being 1,3-dipropyl-8-(3-tetrahydrothienyl)xanthine.

8. A pharmaceutical composition for treating anxiety or fibrillation comprising a CNS stimulation or antifibrillation effective amount of a compound of claim 1 with a pharmaceutically acceptable carrier.

9. A method of treating anxiety in a mammal suffering therefrom comprising administering to said mammal an effective amount of a compound of claim 1.

* * * * *

UNITED STATES PATENT AND TRADEMARK OFFICE
CERTIFICATE OF CORRECTION

PATENT NO. : 4,755,517

DATED : July 5, 1988

INVENTOR(S) : Robert F. Bruns, et al.

It is certified that error appears in the above—identified patent and that said Letters Patent is hereby corrected as shown below:

In column 12 line 26 change "(3-tetrahydrothienyl xanthine" to --(2-tetrahydrothienyl) xanthine--.

Signed and Sealed this

Fourteenth Day of February, 1989

Attest:

DONALD J. QUIGG

Attesting Officer    Commissioner of Patents and Trademarks